(12) United States Patent
Daliri

(10) Patent No.: US 8,166,972 B2
(45) Date of Patent: May 1, 2012

(54) ANTISEPTIC MASK AND METHOD OF USING ANTISEPTIC MASK

(76) Inventor: Shahriar Daliri, Irvine, CA (US)

( * ) Notice: Subject to any disclaimer, the term of this patent is extended or adjusted under 35 U.S.C. 154(b) by 784 days.

(21) Appl. No.: 12/271,584

(22) Filed: Nov. 14, 2008

(65) Prior Publication Data

US 2010/0122703 A1 May 20, 2010

(51) Int. Cl.
*A61M 11/00* (2006.01)
(52) U.S. Cl. .......... 128/204.23; 128/201.25; 128/200.18
(58) Field of Classification Search ............. 128/204.18, 128/201.25, 206.17, 200.18, 205.24, 204.23, 128/203.11
See application file for complete search history.

(56) References Cited

U.S. PATENT DOCUMENTS

| | | | |
|---|---|---|---|
| 1,963,874 A | 6/1934 | Stampe | |
| 2,449,165 A | 9/1948 | Heidbrink | |
| 2,577,606 A * | 12/1951 | Conley | 96/134 |
| 2,818,066 A * | 12/1957 | Glidden | 128/205.24 |
| 3,018,775 A * | 1/1962 | Wilson et al. | 128/203.11 |
| 3,018,776 A * | 1/1962 | Saitta et al. | 128/206.17 |
| 3,556,097 A | 1/1971 | Wallace | |
| 3,932,153 A | 1/1976 | Byrns | |
| 4,141,703 A | 2/1979 | Mulchi | |
| 4,294,599 A | 10/1981 | Grovesteen et al. | |
| 4,354,488 A | 10/1982 | Bartos | |
| 4,444,575 A | 4/1984 | Miller | |
| 4,506,665 A | 3/1985 | Andrews et al. | |
| 4,573,464 A | 3/1986 | Yo | |
| 4,590,951 A * | 5/1986 | O'Connor | 128/204.23 |
| 4,628,927 A | 12/1986 | Ward | |
| 4,636,485 A | 1/1987 | van der Smissen | |
| 4,719,911 A | 1/1988 | Carrico | |
| 4,805,609 A | 2/1989 | Roberts et al. | |
| 4,856,509 A | 8/1989 | Lemelson | |
| 4,932,399 A | 6/1990 | Cappa | |
| 5,140,980 A * | 8/1992 | Haughey et al. | 128/201.25 |
| 5,197,463 A | 3/1993 | Jeshuran | |
| H1316 H | 6/1994 | McGuinness | |
| 5,479,920 A | 1/1996 | Piper et al. | |
| 5,617,844 A * | 4/1997 | King | 128/200.18 |
| 5,878,742 A | 3/1999 | Figueredo et al. | |
| 6,470,882 B1 | 10/2002 | Newhouse et al. | |
| 6,681,765 B2 | 1/2004 | Wen | |
| 6,706,092 B2 | 3/2004 | Rohrbach et al. | |
| 6,748,949 B2 | 6/2004 | Smaldone | |
| 6,799,573 B1 | 10/2004 | Bonner | |
| 7,311,764 B2 * | 12/2007 | Friday et al. | 96/134 |
| 7,380,551 B2 | 6/2008 | Alvey | |
| 2006/0122082 A1 | 6/2006 | Paul | |
| 2007/0163587 A1 | 7/2007 | Teibel | |
| 2008/0083411 A1 | 4/2008 | Guth | |

FOREIGN PATENT DOCUMENTS

| | | |
|---|---|---|
| WO | WO 03092748 | 11/2003 |
| WO | WO 2008009651 | 1/2008 |

* cited by examiner

*Primary Examiner* — Stephen Crow
(74) *Attorney, Agent, or Firm* — David V. Jafari; Jafari Law Group, Inc.

(57) ABSTRACT

The invention is an antiseptic mask, comprising a canister configured to store an antiseptic agent, one or more filters adapted to receive the antiseptic agent and a housing comprising a passageway from an air intake through the one or more filters and to a nose/mouth port. Further, the present invention describes an antiseptic mask and method for treating breathable air contaminated with pathogens through a facial mask filter system using an antiseptic agent to be distributed to a filter through which the air may pass.

17 Claims, 6 Drawing Sheets

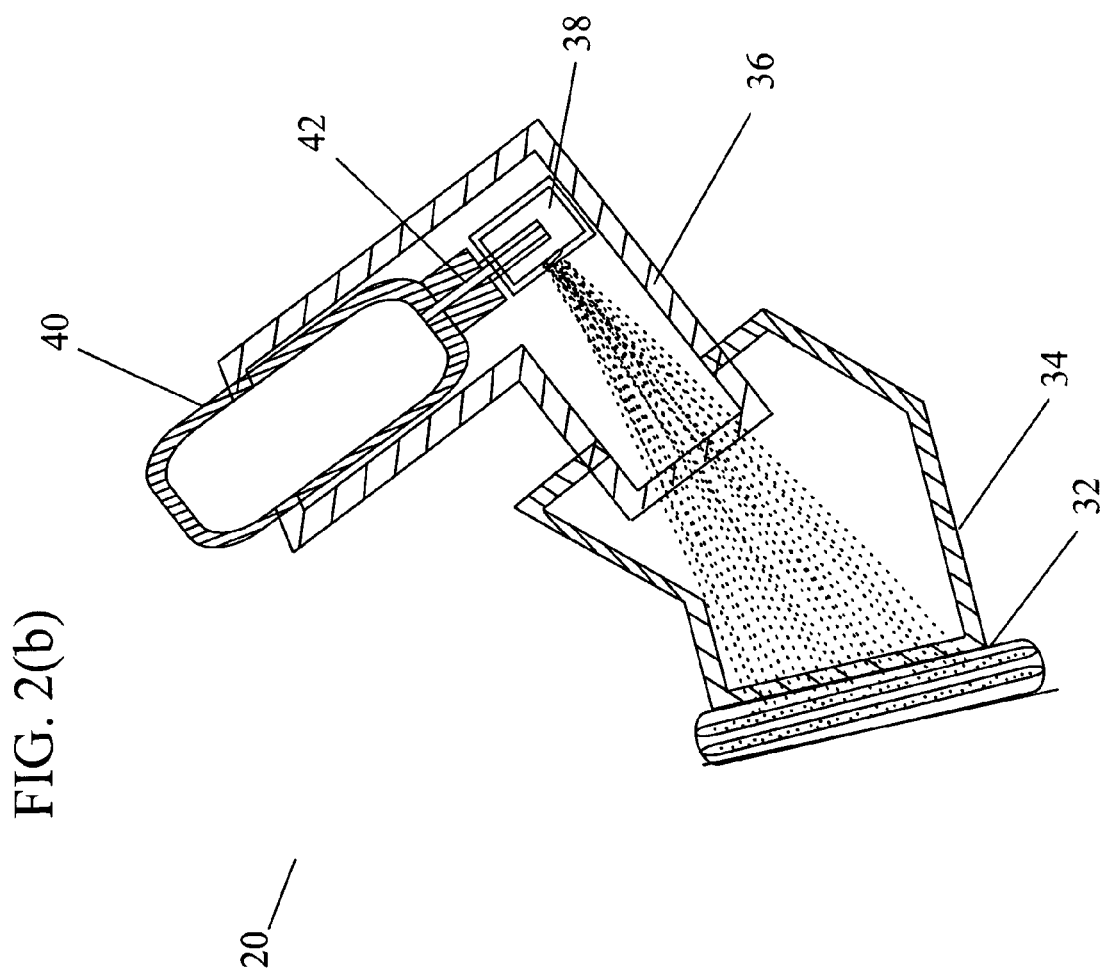

ANTISEPTIC MASK AND METHOD OF USING ANTISEPTIC MASK

TECHNICAL FIELD OF THE INVENTION

The present invention relates in general to an antiseptic mask and, more specifically, to an antiseptic mask comprising an agent that neutralizes pathogens before they enter a user's respiratory system.

COPYRIGHT & TRADEMARK NOTICE

A portion of the disclosure of this patent application may contain material that is subject to copyright protection. The owner has no objection to the facsimile reproduction by any one of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and shall not be construed as descriptive or to limit the scope of this invention to material associated only with such marks.

BACKGROUND OF THE INVENTION

Air treatment systems provide a means for improving the quality of breathable air. These devices typically operate in one of two ways: by filtering out particulates and pathogens from the air, or by neutralizing a pathogenic threat in the air.

Air filtration systems may remove particulate or pathogenic matter from the air in a variety of ways. Typical filter-based purification systems trap or block airborne particles from passage through the filter. The type and size of the particulate or pathogenic matter filtered out of the air by an air filtration system is dependent upon the type of filter used, the number of filters used, and the complexity of the system, among other factors. As such, the effectiveness of a filtration system is frequently dependent upon its cost.

While air filtration systems may be used to purify the environment of a large structure, such as an air filtration system in a commercial building, there is a need for personal, mobile filtration devices. Mobile air filtration systems, such as gas masks, filter air inhaled by a user. Typical gas masks include a complicated filtration system in order to protect a user from a wide variety of contaminants. As such, in order to protect from a wide variety of contaminants, these filtration systems are often expensive, heavy and cumbersome.

In the alternative, other types of mobile filtration systems are typically comprised of a disposable mask with a cup-shaped member to place over the nose and mouth of the user. These face mask systems are typically inexpensive and lightweight. However, in the event of a pathogen threat, these masks do not provide the pathogen-filtration or neutralization components necessary to protect the user, as they are designed only for the removal of particulate matter. Furthermore, these masks do not create a pressurized seal to the face, which may allow contaminants to seep around the mask, rendering the mask ineffective.

In contrast to filtration systems, airborne pathogenic neutralization systems neutralize bacteria and viruses in the air. By rendering the pathogen benign, a pathogen poses no threat to the user, and thus there is no need to filter out the contaminant from the air. Photocatalytic oxidation, for example, oxidizes and degrades organic contaminants, thereby rendering bacteria and viruses benign. Photocatalytic oxidation, however, is an expensive process, as it is energy intensive and would be impractical to utilize in a mobile system. As such, there is a need for an airborne pathogenic neutralization system that may be inexpensive, lightweight and portable.

Thus, there is a need for a mobile, lightweight, inexpensive air neutralization system or self-contained breathing apparatus that can neutralize airborne pathogens before they harm the body. Specifically, there is a need for an antiseptic mask comprising an agent that neutralizes pathogens before they enter a user's respiratory system. It is to these ends that the present invention has been developed.

SUMMARY OF THE INVENTION

To minimize the limitations in the prior art, and to minimize other limitations that will be apparent upon reading and understanding the present specification, the present invention describes an antiseptic mask and method for treating breathable air, contaminated with pathogens, through a facial mask neutralization system using an antiseptic agent to be distributed to a filter through which the air may pass.

An apparatus in accordance with the present invention may comprise: a canister configured so as to store an antiseptic agent that may neutralize specific pathogens, one or more filters that receive and store the antiseptic agent, and a housing that intakes air through a possible air inlet, then through a passageway, and then through a filter or filters to the user's nose and/or mouth. The air inlet leading to the passageway may be one-directional. The apparatus may then dispose of the user's exhaled air through an air passage outlet, that may be one-directional as well.

The device may comprise filters that are disposable and changeable. The housing may be secured over the nose and/or mouth of the user. Furthermore, the housing may include a flange on the inside perimeter so as to assist in providing an air-tight pressurized seal. A strap may be provided on the mask so as to secure the mask to the user's face.

Additionally, an apparatus in accordance with the present invention may have a canister to house an antiseptic agent that is interchangeable, and may be removed from the mask and replaced with another canister that is also configured to store an antiseptic agent, or the canister may be designed to be refillable with an agent. The canister may be filled with a variety of agents, so as to be selected and administered on the basis of what particular contaminates are present. The canister may be activated in a variety of manners so as to inject the agent onto the filter or filters.

Moreover, a method in accordance with the present invention may comprise the steps of: providing a means for the antiseptic agent to be applied to one or more filters, providing a passageway so as to allow air in the environment to pass through filters which may treat the air before it is inhaled by the user, and possibly providing a passageway for the air exhaled by the user to exit the system. Furthermore, the method includes the application of the agent to a filter by spraying the agent onto a filter, which may absorb and store the agent. In addition the method may provide for an antiseptic agent to be housed in interchangeable canisters that may be refilled with an agent, or changed with other canisters that may house different agents selectable on the basis of the type of contamination in the environment. Moreover, the filters may be replaceable and interchangeable with other filters compatible to receive an antiseptic agent.

It is an objective of the present invention to provide the means of treating pathogen-contaminated air.

It is another objective of the present invention to provide a portable and lightweight means of treatment of airborne pathogens for a user.

It is yet another objective of the present invention to provide the means of treating pathogen-contaminated air by treating filters with an agent, through which external air may pass en route to the user's respiratory system.

It is yet another objective of the present invention to potentially provide pathogen-neutralized treated air to a user in the presence of a contamination.

Finally, it is yet another objective of the present invention to provide a lower-cost means of accomplishing these objectives.

These and other advantages and features of the present invention are described herein with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 2(b) illustrates chemical agent dispersal in a cross-sectional view of an exemplary embodiment of a pathogen neutralization system taken along line A-A of FIG. 1.

DETAILED DESCRIPTION OF THE DRAWINGS

In the following discussion that addresses a number of embodiments and applications of the present invention, reference is made to the accompanying drawings that form a part hereof, where depictions are made, by way of illustration, of specific embodiments in which the invention may be practiced. It is to be understood that other embodiments may be utilized and changes may be made without departing from the scope of the present invention.

Figure 1A:
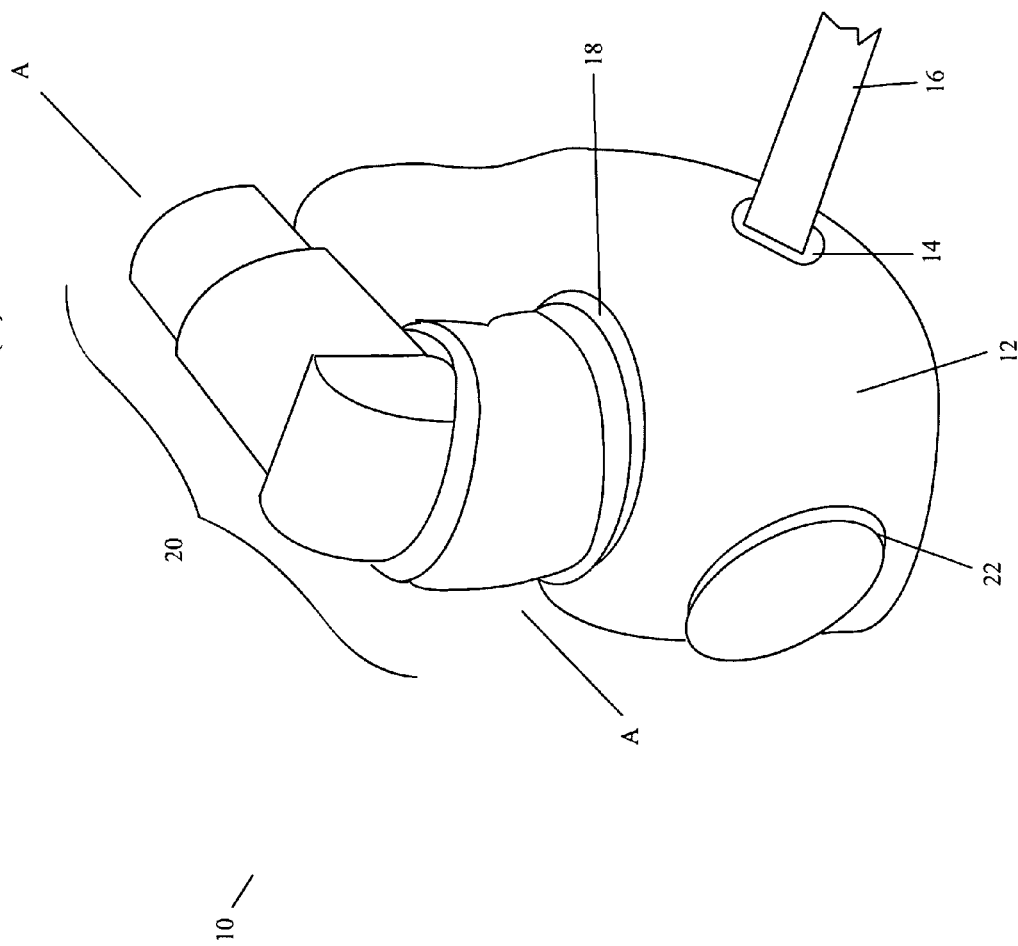
FIG. 1(a) illustrates a perspective view of an exemplary embodiment of an antiseptic mask.
Figure 1B:
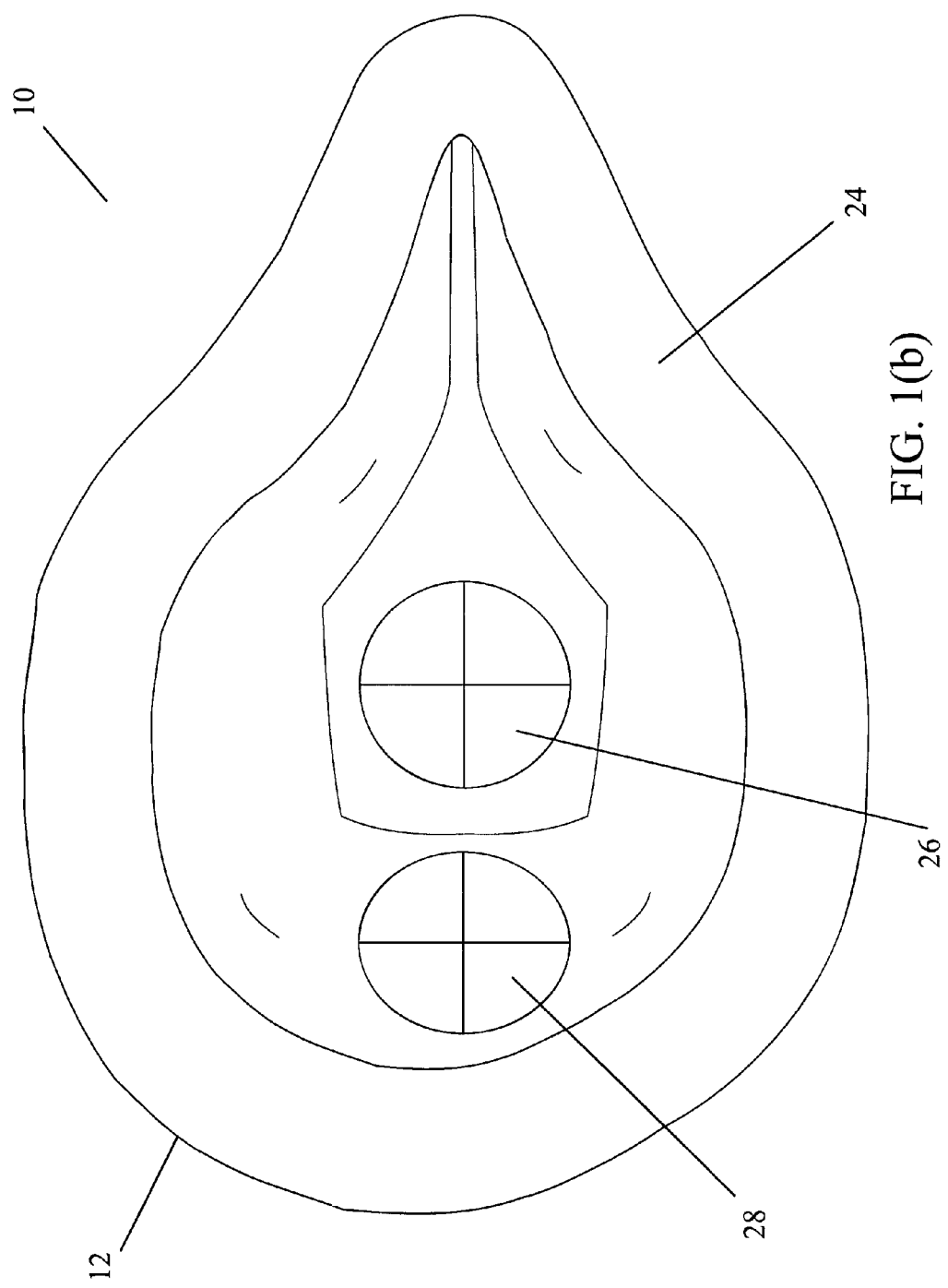
FIG. 1(b) illustrates an under-side view of the inside of an exemplary embodiment of an antiseptic mask.

FIG. 1(a) illustrates a perspective view of an exemplary embodiment of an antiseptic mask. FIG. 1(b) illustrates an under-side view of the inside of an exemplary embodiment of an antiseptic mask.

FIG. 1(a) shows antiseptic mask 10, which contains mask housing 12, connecting hook 14, strap 16, air inlet 18, pathogen neutralization system 20, and air outlet 22. FIG. 1(b) shows antiseptic mask 10, which contains inner flange 24, inlet control valve 26, and outlet control valve 28. Antiseptic mask 10 is designed to regulate the inhalation and exhalation of air by user through air inlet 18 and air outlet 22, respectively, but to also allow for the treatment of air inhaled by user through pathogen neutralization system 20.

Mask housing 12 is the main body of antiseptic mask 10. Mask housing 12 is an object designed to be placed upon a user's mouth or the nasal region of the user's face. In an exemplary embodiment, mask housing 12 is shaped such that it may couple with the mouth and nasal region of a user's face, but also have a depth such that there is an aero-chamber of breathable air which may be contained between mask housing 12 and the user's face when antiseptic mask 10 is in use.

Mask housing 12 may be composed of a variety of materials; including polypropylene, polyethylene, neoprene, or any other material that is sufficiently impervious to pathogens for at least the designed use life of antiseptic mask 10. The material used in the composition of mask housing 12 may be rigid such as to maintain a pre-molded shape, but yet flexible enough to bend and adapt so as to mold to the face of the user. In an exemplary embodiment, mask housing 12 may be adapted so as to be able to mold to a user's face when used. When pressed against a user's face, mask housing 12 may create a pressurized seal between antiseptic mask 10 and the user's face, thereby creating a mouth and nasal aero-chamber such that breathable air may only enter antiseptic mask 10 through air inlet 18 and exit through air outlet 22, respectively (discussed in detail below).

Inner flange 24, illustrated in FIG. 1(b), is an inner flap connected to mask housing 12 designed to rest upon and create a pressurized seal with a user's face during exemplary use of antiseptic mask 10. In an exemplary embodiment, inner flange 24 is an extension of mask housing 12 folded in on itself, thereby increasing the effectiveness of mask housing 12 by molding to the contours of a user's face and clinging thereto, thus creating a pressurized seal. In another embodiment, however, antiseptic mask 10 may not include inner flange 24, and thus the inclusion of inner flange 24 should not be interpreted so as to narrow the scope of the present invention.

Connecting hook 14 couples mask housing 12 to strap 16. In a preferred embodiment, antiseptic mask 10 may contain more than one connecting hook 14 located on surface of mask housing 12. Additionally, connecting hook 14 may rotate or pivot so as to allow strap 16 to stretch in a plurality of directions. Strap 16 may be used to couple antiseptic mask 10 to a user's face. In an exemplary embodiment, strap 16 may be placed around a user's head so as to press antiseptic mask 10 firmly against a user's face, thereby creating a pressurized seal. Strap 16 may be elastic in nature so as to stretch and tighten around a user's head, or may include a buckle so as to allow a user to manually tighten strap 16 in order to firmly press antiseptic mask 10 against a user's face. Other embodiments of antiseptic mask 10, however, may not include connecting hook 14 or strap 16, and thus their inclusion here should not be interpreted so as to narrow the scope of the present invention.

Air inlet 18 is a passageway in mask housing 12 designed so as to allow for the intake of air. The flow of air through air inlet 18, in a preferred embodiment, is one directional, meaning that air may only flow into antiseptic mask 10 through air inlet 18, illustrated in FIG. 2(a) and described in detail below, and may not evacuate antiseptic mask 10 through air inlet 18. Additionally, filters 30 (illustrated in FIGS. 2 and 3) may be placed in air inlet 18 for the treatment of air (discussed in detail below). The flow of air through air inlet 18 is governed by inlet control valve 26.

Inlet control valve 26 is a control mechanism coupled to air inlet 18 and mask housing 12 so as to prevent the expulsion of air through air inlet 18. Inlet control valve 26, in an exemplary embodiment, governs the flow of air entering antiseptic mask 10 through air inlet 18 and prevents the expulsion of air through air inlet 18. In a preferred embodiment inlet control valve 26 is pulled open by the suction created when a user breathes in while wearing antiseptic mask 10, allowing air to be inhaled through air inlet 18. Furthermore, in a preferred embodiment, inlet control valve 26 is pushed closed by the pressure created when the user exhales, thereby prohibiting air to be evacuated through air inlet 18. Thus, exemplary functionality of inlet control valve 26 would make air inlet 18 one-directional in nature, allowing only for the in-flow of air.

Air outlet 22 is a passageway in mask housing 12 designed so as to allow the outflow of air. The flow of air through air outlet 22, in a preferred embodiment, is one-directional, allowing air to only flow out of antiseptic mask 10 through air outlet 22, and not infiltrate antiseptic mask 10 through air outlet 22. Air flow through air outlet 22 is illustrated in FIG. 2(a).

Outlet control valve 28 is a control mechanism coupled to air outlet 22 and mask housing 12 so as to prevent the inhalation of air through air outlet 22. Outlet control valve 28, in an exemplary embodiment, governs the flow of air exiting antiseptic mask 10 through air outlet 22 and prevents the inhalation of air through air outlet 22. In a preferred embodiment, when a user breathes out while wearing antiseptic mask 10, outlet control valve 28 is pushed open, allowing air to be exhaled through air outlet 22. However, in a preferred embodiment, when the user breathes in, outlet control valve 28 is pulled closed by the suction pressure created in the aero-chamber of antiseptic mask 10, thereby prohibiting air to be inhaled through air outlet 22. Thus, exemplary functionality of outlet control valve 28 would make air outlet 22 one-directional in nature, allowing only for the outflow of air.

The governance of the flow of air in and out of antiseptic mask 10 may be achieved by means other than inlet and outlet control valves. While the preferred embodiment of antiseptic mask 10 may include control valves, it should not be interpreted so as to limit or narrow the scope of the present invention.

Figure 2A:
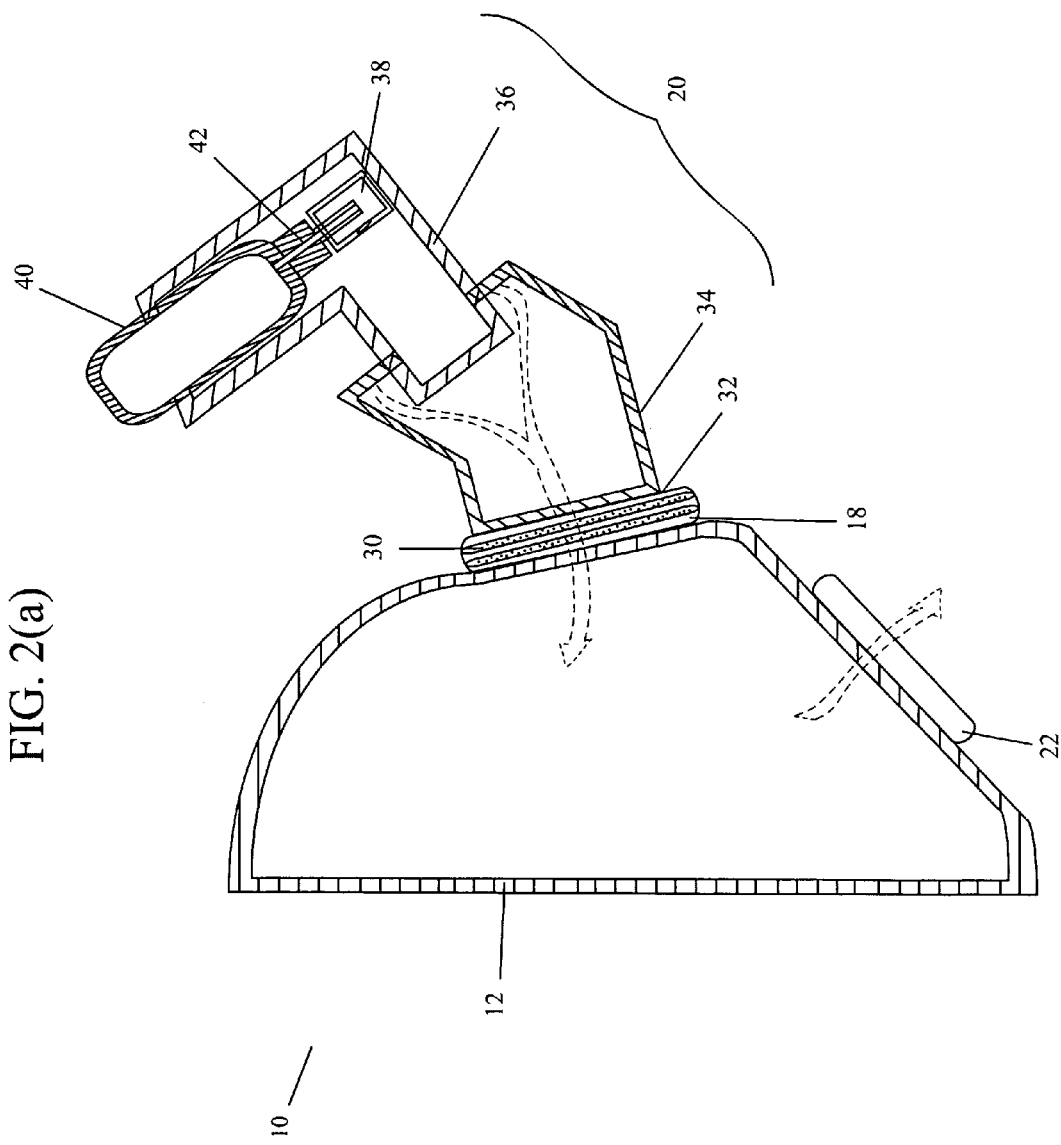
FIG. 2(a) illustrates air flow in a cross-sectional view of an exemplary embodiment of an antiseptic mask taken along line A-A of FIG. 1.

In the present embodiment, the inhalation and expulsion of air by a user through antiseptic mask 10 are achieved through different passages in mask housing 12 as illustrated in FIG. 2(a). By diverting the expulsion of air through air outlet 22, the effectiveness of the treatment agent applied to filters located in air inlet 18 may decrease more moderately over time than if air was expelled through air inlet 18, as the amount of particulate matter potentially trapped in the filters is lessened (described in detail below). In another embodiment, antiseptic mask 10 may contain only one passage for both the inhalation and expulsion of air. Thus, the inclusion of multiple passages for the inhalation and expulsion of air from antiseptic mask 10 should not be interpreted so as to narrow or limit the scope of the present invention.

Pathogen neutralization system 20 may be used to treat air inhaled prior to its passage through air inlet 18. Pathogen neutralization system 20 may be comprised of a number of components (described in detail below). Pathogen neutralization system 20 disperses an antiseptic agent onto filters contained in air inlet 18, as illustrated in FIG. 2(b). When a user breathes in, air may pass through pathogen neutralization system 20, which may neutralize pathogens in the air. In order for all inhaled air to be treated, pathogen neutralization system 20 may be securely coupled to air inlet 18, thereby requiring all air inhaled to pass through the filters contained in air inlet 18.

In all embodiments of antiseptic mask 10, inhalation of air must pass through pathogen neutralization system 20 should air be treated. If mask housing 12 and inner flange 24 are not pressurized against a user's face, then air may be inhaled by a user that did not pass through filters contained in air inlet 18 and pathogen neutralization system 20. In the exemplary usage of antiseptic mask 10, antiseptic mask 10 should be worn such that there exists a pressurized seal between antiseptic mask 10 and a user's face, in order for air inhalation to be channeled solely through air inlet 18.

FIG. 2(a) illustrates air flow in a cross-sectional view of an exemplary embodiment of an antiseptic mask taken along line A-A of FIG. 1. FIG. 2(b) illustrates chemical agent dispersal in a cross-sectional view of an exemplary embodiment of a pathogen neutralization system 20 taken along line A-A of FIG. 1. FIG. 2 shows antiseptic mask 10, which includes mask housing 12, air inlet 18, air outlet 22, filters 30, and pathogen neutralization system 20, which includes inlet cap 32, air passage tube 34, canister housing 36, agent dispersal apparatus 38, canister 40, and canister nozzle 42.

Figure 3:
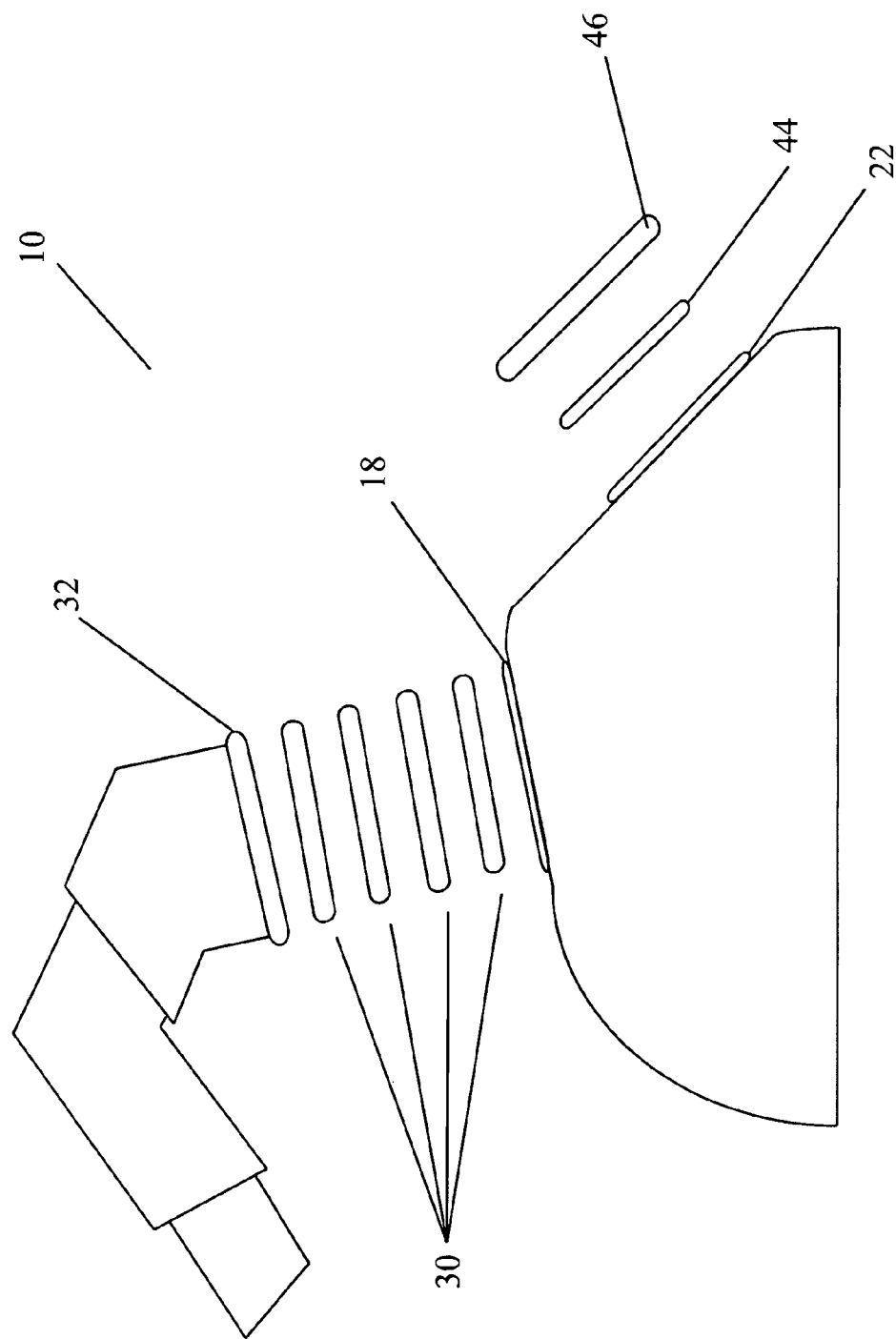
FIG. 3 is an exploded side view of an exemplary embodiment of an antiseptic mask.

FIG. 3 is an exploded side view of an exemplary embodiment of an antiseptic mask. FIG. 3 shows antiseptic mask 10, a plurality of filters 30 situated in air inlet 18 enclosed by inlet cap 32, and outlet valve support 44, which is situated in air outlet 22 and enclosed by outlet cap 46.

A plurality of filters 30 may be utilized in exemplary functionality of antiseptic mask 10. In a preferred embodiment of the present invention, four filters 30 may be utilized according to their placement in air inlet 18. Note, however, that the number of filters 30 utilized in a preferred embodiment should not be interpreted so as to narrow or limit the scope of the present invention. In exemplary functionality, an antiseptic agent may be dispersed upon filter 30 such that air may be treated by its passage through filter 30 (discussed in detail below).

The composition, type and thickness of the filter 30 used in antiseptic mask 10 may vary. Typical filter media such as paper, foam, synthetics or cotton may be utilized in the composition of filter 30, however this list is not exhaustive and should not be interpreted so as to narrow the scope of the present invention. A key aspect of the filter media utilized in filter 30, however, is that a antiseptic agent may be sufficiently dispersed upon filter 30 such that air passing through filter 30 may be adequately treated by the antiseptic agent. Additionally, the composition of filter 30 may be tailored as to the antiseptic agent used in antiseptic mask 10 and towards the pathogen targeted for neutralization. The composition, type and thickness of filter 30, however, may be limited such that a user need be able to inhale air through filter 30. Thus, in an exemplary embodiment of antiseptic mask 10, filter 30 may have a composition, type and thickness such that a user may adequately breathe through filter 30 without too much exertion, but that an antiseptic agent may be sufficiently dispersed upon filter 30 such that air may be treated by the antiseptic agent.

The size and shape of filter 30 is dependent upon the dimensions of air passage tube 34. In order to meet the desired functionary purpose of antiseptic mask 10, filter 30 need completely obstruct air inlet 18 such that any air or particulate matter passing through air inlet 18 must pass through filter 30. Additionally, filters 30 may be disposable, allowing a user to replace filter 30 when antiseptic mask 10 is not in use. The replacement of filter 30 may increase the effectiveness of antiseptic mask 10 during use, as fresh filters may allow for an increased rate of air passage through the filters, due to removal of obstructions caused by trapped particulate matter and buildup of the antiseptic agent, in addition to potentially increasing the antiseptic agent's effectiveness by enabling the treatment of a heightened volume of pathogens or injurious particulate matter.

Pathogen neutralization system 20, as previously described, may provide a means for the treatment of air inhaled through air inlet 18. In the present embodiment of antiseptic mask 10, pathogen neutralization system 20 may comprise inlet cap 32, air passage tube 34, canister housing 36, agent dispersal apparatus 38, canister 40, and canister nozzle 42.

Inlet cap 32 is a component of pathogen neutralization system 20. Inlet cap 32 separates air inlet 18 from air passage tube 34. Inlet cap 32 may be securely attached to or detached from air inlet 18. In an exemplary embodiment, inlet cap 32 is securely coupled to air passage tube 34 such that pathogen neutralization system 20 may be detached from air inlet 18. In an exemplary embodiment, should inlet cap 32 be securely attached to air inlet 18, air may only enter air inlet 18 through pathogen neutralization system 20. When inlet cap 32 is securely attached to air inlet 18, pathogen neutralization system 20 may disperse an antiseptic agent, via agent dispersal apparatus 38, upon filter 30 situated in air inlet 18. Filters 30, situated in air inlet 18, may be replaced when inlet cap 32 is detached from air inlet 18.

In a preferred embodiment, inlet cap 32 may be perforated such that a antiseptic agent may pass through inlet cap 32 from pathogen neutralization system 20 to filters 30 situated in air inlet 18, but also such that inlet cap 32 may help to block particulate matter from reaching filter 30. In another embodiment, however, inlet cap 32 may simply be the means to couple and disconnect pathogen neutralization system 20 with air inlet 18, providing no obstruction in the opening between air passage tube 34 and air inlet 18, and thereby not blocking particulate matter.

Air passage tube 34 is a component of pathogen neutralization system 20. In a preferred embodiment, air passage tube 34 is securely coupled at its proximal end to inlet cap 32. When activated, an antiseptic agent may be sprayed through air passage tube 34 onto filters 30 contained in air inlet 18. Additionally, air passage tube 34 may be securely coupled to canister housing 36 at its distal end, while maintaining air apertures such that when a user breathes in, air enters pathogen neutralization system 20 through air passage tube 34 via said apertures at the distal end of air passage tube 34. In another embodiment, air passage tube 34 may contain openings on its sidewall, as opposed to the distal end of air passage tube 34, such that air may be inhaled into and through pathogen neutralization system 20.

Canister housing 36 is an additional component of pathogen neutralization system 20. Canister housing 36 contains agent dispersal apparatus 38 and may receive and retain canister 40. Canister housing 36 is designed so that canister 40 may be securely attached to and detached from agent dispersal apparatus 38. Canister housing 36 is securely coupled to air passage tube 34 such that air may enter air passage tube 34 via apertures.

Agent dispersal apparatus 38 sprays an antiseptic agent contained in canister 40 onto filters 30 in air inlet 18. Agent dispersal apparatus 38 is situated in canister housing 36 such that canister nozzle 42 on canister 40 may be securely affixed to, and unfastened from, canister housing 36. In a preferred embodiment, agent dispersal apparatus 38 operates such that when canister 40 is depressed inside canister housing 36, an antiseptic agent contained in canister 40 is atomized by agent dispersal apparatus 38 and dispersed onto filters 30. However, in other embodiments, activation of agent disbursement apparatus 38 may be achieved in a variety of manners, and this preferred embodiment should not be interpreted so as to narrow or limit the scope of the present invention.

Canister 40 may be securely attached to and detached from canister housing 36. Canister 40 may contain an antiseptic agent designed to neutralize airborne pathogens. In a preferred embodiment, canister 40 may be replaced, disposed of, or swapped for another compatible canister. In an exemplary use, should all of the antiseptic agent in canister 40 be exhausted through use of antiseptic mask 10, canister 40 may be detached from canister housing 36 and replaced with a new canister. In another embodiment, canister 40 may be refilled with an antiseptic agent. An advantage of canister 40 being removable is that canister 40 may be filled with alternative antiseptic agents that perform different functions. Thus, canister 40, and therefore the antiseptic agent, may be selected and used in antiseptic mask 10 to target the particular contaminate present. In yet another embodiment of antiseptic mask 10, canister 40 may be fixed to canister housing 36 and agent dispersal apparatus 38, but may be refillable.

Canister nozzle 42 may couple canister 40 to agent dispersal apparatus 38. Canister nozzle 42 may be situated on canister 40. In a preferred embodiment, upon activation, an antiseptic agent may transfer from canister 40 through canister nozzle 42 to agent dispersal apparatus 38.

Outlet cap 46 may be securely attached to and detached from air outlet 22. In an exemplary embodiment, outlet cap 46 keeps outlet valve support 44 in place. Outlet valve support 44 aids outlet control valve 28 in preventing the intake of air through air outlet 22. Outlet valve support 44 acts as a counter-weight for outlet control valve 28, wherein outlet control valve 28 is pushed shut when the user is not breathing out. Should a user breath out, pressure inside antiseptic mask 10 is increased, thereby pushing outlet control valve 28 open and lifting outlet valve support 44 away from mask housing 12. When a user breathes in, however, outlet control valve 28 is pushed shut by outlet valve support 44, as the pressure inside mask housing 12 is decreased. In the preferred embodiment, outlet valve support 44 aids in the prolonged use of antiseptic mask 10, as it reduces decreases in performance of outlet control valve 28 due to deformity from extended use. In another embodiment of antiseptic mask 10, outlet valve support 44 and outlet cap 46 may not be included, as outlet control valve 28 may open and shut independently and be more resistant to deformity from extended use.

Figure 4:
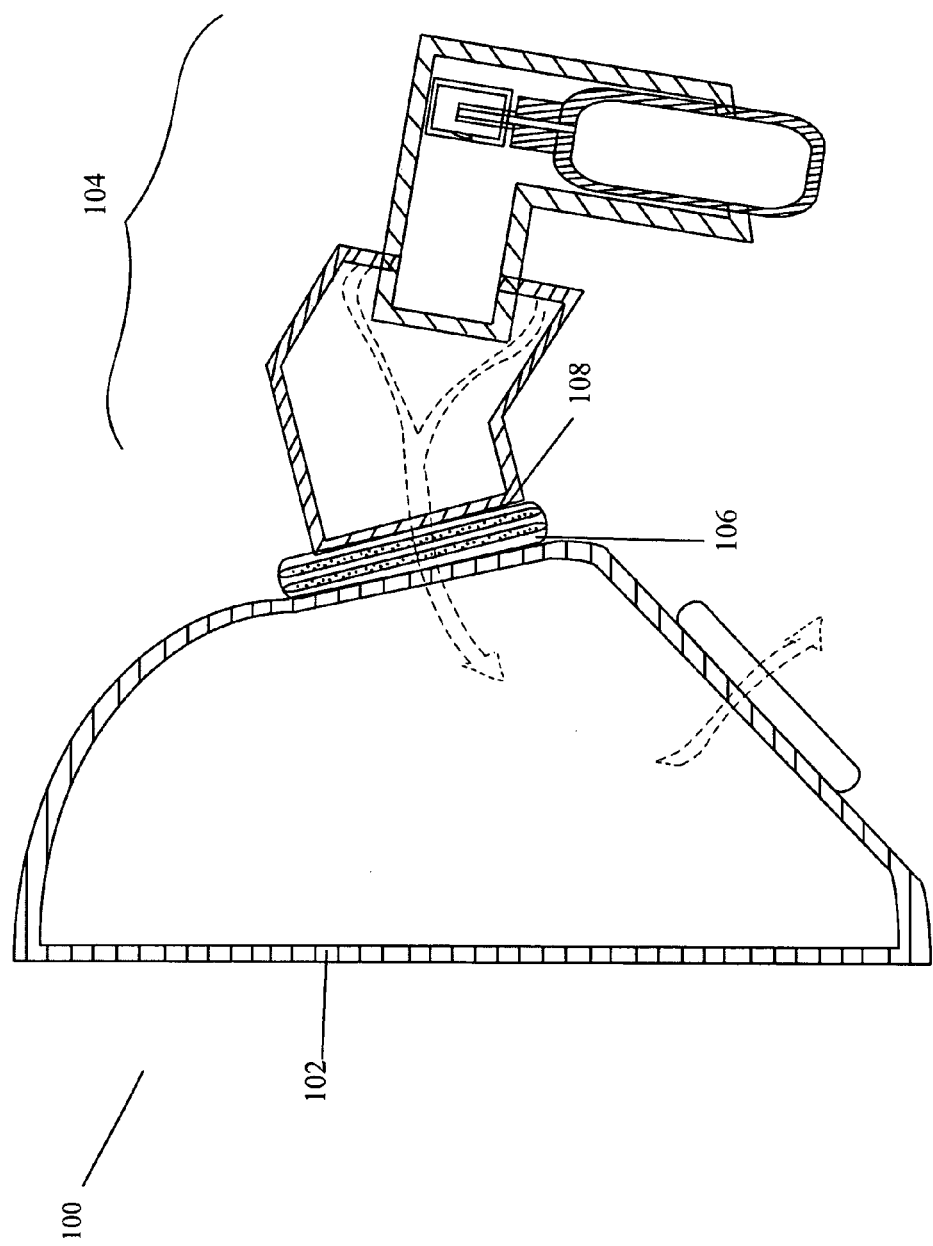
FIG. 4 illustrates air flow in a cross-sectional view of an alternative embodiment of an antiseptic mask.

FIG. 4 illustrates air flow in a cross-sectional view of an alternative embodiment of an antiseptic mask. FIG. 4 shows antiseptic mask 100, which includes mask housing 102, pathogen neutralization system 104, air inlet 106, and inlet cap 108. In FIG. 4, pathogen neutralization system 104 may rotate in orientation around air inlet 106 via inlet cap 108. Therefore, the orientation of pathogen neutralization system 104 with respect to mask housing 102 should not be interpreted so as to narrow the scope of the present invention.

An antiseptic mask and method has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching. It is intended that the scope of the invention not be limited by this detailed description, but by the claims and the equivalents to the claims.

What is claimed is:
1. A mask, comprising:
 a canister housing adapted to receive a canister containing a fluid agent;
 a filter;
 a passageway adapted to fluidly couple the fluid agent from the canister housing to an input of the filter means to inject said fluid agent onto said filter;
 an air intake adapted to direct external air to the input of the filter; and a facial housing adapted to fit over a user's oral and nasal facial regions, and which includes an intake port adapted to receive the filtered fluid agent-treated air that is generated at an output of the filter; wherein said canister is activated to inject said agent onto said filter.

2. The mask of claim 1, wherein said canister can be interchanged within the canister housing and may be swapped out of the mask for another canister containing a fluid agent.

3. The mask of claim 1, wherein said activation includes depression of said canister.

4. The mask of claim 1, wherein said filter may be replaced with another compatible filter configured to receive a fluid agent.

5. The mask of claim 1, wherein said filter are disposable.

6. The mask of claim 1, wherein said air intake is unidirectional.

7. The mask of claim 1, wherein said facial housing includes an air outlet.

8. The mask of claim 7, wherein said air outlet is unidirectional.

9. The mask of claim 1, wherein said agent is anti-pathogenic.

10. The mask of claim 1, wherein said facial housing includes a strap.

11. The mask of claim 1, wherein said facial housing includes an inner flange.

12. A method for the treatment of air, comprising the steps of:

providing a means for the application of a fluid agent to a filter via;

a canister housing adapted to receive a canister containing a fluid agent;

a filter; and a passageway adapted to fluidly couple the fluid agent from the canister housing to an input of the filter; and providing a passageway to allow external air to pass through the treated filter via an air intake adapted to direct external air to the input of the filter; and a facial housing adapted to fit over a user's oral and nasal facial regions, and which includes an intake port adapted to receive the filtered fluid agent-treated air that is generated at an output of the filter.

13. The method of claim 12, wherein application of the fluid agent comprises spraying the agent onto the filter.

14. The method of claim 12, wherein an outlet passageway for exhalation is provided.

15. The method of claim 12, wherein the fluid agent is housed in an interchangeable canister that may be swapped for another canister containing a fluid agent.

16. The method of claim 12, wherein said filter may be interchangeable for other compatible filters configured to receive a fluid agent.

17. An mask, comprising:

a canister housing adapted to receive a canister containing a fluid agent;

a filter;

a passageway adapted to fluidly couple the fluid agent from the canister housing to an input of the filter;

an air intake adapted to direct external air to the input of the filter;

wherein the air intake is a unidirectional air passageway;

wherein said canister is activated to inject said agent onto said filter and a facial housing adapted to fit over a user's oral and nasal facial regions, and which includes an intake port adapted to receive the filtered fluid agent-treated air that is generated at an output of the filter;

wherein the facial housing further comprises:

an air outlet that is a unidirectional air passageway;

a strap; and an inner flange.

* * * * *